(12) United States Patent
Diwan et al.

(10) Patent No.: US 9,216,092 B2
(45) Date of Patent: Dec. 22, 2015

(54) TISSUE PROSTHESIS AND METHOD OF, AND EQUIPMENT FOR, FORMING A TISSUE PROSTHESIS

(75) Inventors: Ashish D. Diwan, Syndney (AU); Zoran Milijasevic, Bayview (AU); Johnathon Choi, Carlinford (AU); Sandra Fisher, Syndney (AU)

(73) Assignee: SPINECELL PRIVATE LIMITED

( * ) Notice: Subject to any disclaimer, the term of this patent is extended or adjusted under 35 U.S.C. 154(b) by 461 days.

(21) Appl. No.: 13/561,899

(22) Filed: Jul. 30, 2012

(65) Prior Publication Data

US 2012/0330221 A1    Dec. 27, 2012

Related U.S. Application Data

(60) Division of application No. 12/017,430, filed on Jan. 22, 2008, now abandoned, which is a continuation of application No. PCT/AU2006/001176, filed on Aug. 15, 2006.

(60) Provisional application No. 60/708,670, filed on Aug. 15, 2005.

(51) Int. Cl.
*A61M 29/00* (2006.01)
*A61F 2/44* (2006.01)
(Continued)

(52) U.S. Cl.
CPC .............. *A61F 2/441* (2013.01); *A61F 2/4611* (2013.01); *A61B 17/8827* (2013.01);
(Continued)

(58) Field of Classification Search
CPC .................. A61F 2/441; A61F 2/4611; A61F 2002/30014; A61F 2002/30563; A61F 2002/467; A61F 2210/0085; A61F 2002/30561; A61F 2002/30069; A61F 2002/30235; A61F 2002/444; A61F 2002/4627; A61F 2250/0098; A61F 2002/3008; A61F 2002/3024; A61F 2002/30583; A61F 2002/4495; A61F 2002/4663; A61F 2002/4685; A61F 2230/0069; A61B 17/8827; A61B 17/12031
USPC ........... 606/191, 192, 195, 92, 93; 623/17.11, 623/17.12, 27.32; 604/43, 45
See application file for complete search history.

(56) References Cited

U.S. PATENT DOCUMENTS 3,918,443 A    11/1975  Vennard et al.
4,364,392 A    12/1982  Strothers et al.
(Continued)

FOREIGN PATENT DOCUMENTS

FR    2871679 A    12/2005
WO    WO 99/02108 A    1/1999
(Continued)

OTHER PUBLICATIONS

International Search Report and Written Opinion of PCT Application No. PCT/AU2006/001176, Nov. 17, 2006, 14 pages total.

*Primary Examiner* — Jing Ou
(74) *Attorney, Agent, or Firm* — Jerry R. Potts; James R. McDaniel

(57) ABSTRACT

A tissue prosthesis 100 comprises an envelope 38 of a biologically inert, elastically deformable material capable of being expanded to conform to an interior surface of a cavity 36 formed at a site 10 in a patient's body. A filler material 60 is received in a fluent state in the envelope 38. The filler material 60 is of the same class of material as the envelope 38 to form, when cured, together with the envelope 38, a unified structure.

5 Claims, 12 Drawing Sheets

(51) Int. Cl.
  *A61F 2/46* (2006.01)
  *A61B 17/88* (2006.01)
  *A61F 2/30* (2006.01)

(52) U.S. Cl.
  CPC  *A61F 2002/3008* (2013.01); *A61F 2002/3024* (2013.01); *A61F 2002/30069* (2013.01); *A61F 2002/30235* (2013.01); *A61F 2002/30561* (2013.01); *A61F 2002/30583* (2013.01); *A61F 2002/444* (2013.01); *A61F 2002/4495* (2013.01); *A61F 2002/467* (2013.01); *A61F 2002/4627* (2013.01); *A61F 2002/4663* (2013.01); *A61F 2002/4685* (2013.01); *A61F 2210/0085* (2013.01); *A61F 2230/0069* (2013.01); *A61F 2250/0098* (2013.01)

(56) References Cited

U.S. PATENT DOCUMENTS

| | | | |
|---|---|---|---|
| 4,545,367 A | | 10/1985 | Tucci |
| 5,549,679 A | * | 8/1996 | Kuslich ............... 623/17.12 |
| 5,779,672 A | * | 7/1998 | Dormandy, Jr. ......... 604/99.04 |
| 6,306,177 B1 | | 10/2001 | Felt et al. |
| 6,443,988 B2 | | 9/2002 | Felt et al. |
| 6,786,887 B2 | * | 9/2004 | Roychowdhury et al. . 604/96.01 |
| 6,969,404 B2 | | 11/2005 | Ferree |
| 7,001,431 B2 | | 2/2006 | Bao et al. |
| 7,025,771 B2 | | 4/2006 | Kuslich et al. |
| 7,077,865 B2 | | 7/2006 | Bao et al. |
| 7,144,407 B1 | * | 12/2006 | Lasersohn ............... 606/192 |
| 7,713,301 B2 | | 5/2010 | Bao et al. |
| 7,766,965 B2 | | 8/2010 | Bao et al. |
| 2002/0138091 A1 | | 9/2002 | Pflueger |
| 2003/0033017 A1 | | 2/2003 | Lotz et al. |
| 2003/0195628 A1 | | 10/2003 | Bao et al. |
| 2003/0220649 A1 | | 11/2003 | Bao et al. |
| 2003/0229372 A1 | | 12/2003 | Reiley et al. |
| 2005/0027358 A1 | | 2/2005 | Suddaby |
| 2005/0043808 A1 | * | 2/2005 | Felt et al. ............... 623/20.14 |
| 2005/0090901 A1 | * | 4/2005 | Studer ................. 623/17.12 |
| 2005/0245938 A1 | | 11/2005 | Kochan |
| 2006/0009851 A1 | * | 1/2006 | Collins et al. ........... 623/17.16 |
| 2006/0247780 A1 | * | 11/2006 | Bert ..................... 623/17.16 |
| 2006/0293750 A1 | * | 12/2006 | Sherman et al. ......... 623/17.12 |
| 2007/0299460 A9 | * | 12/2007 | Boucher et al. ........... 606/191 |

FOREIGN PATENT DOCUMENTS

| | | |
|---|---|---|
| WO | WO 02/30338 A | 4/2002 |
| WO | WO 03/047472 A | 6/2003 |
| WO | WO 2005/002474 A | 1/2005 |
| WO | WO 2006/092015 A | 9/2006 |

\* cited by examiner

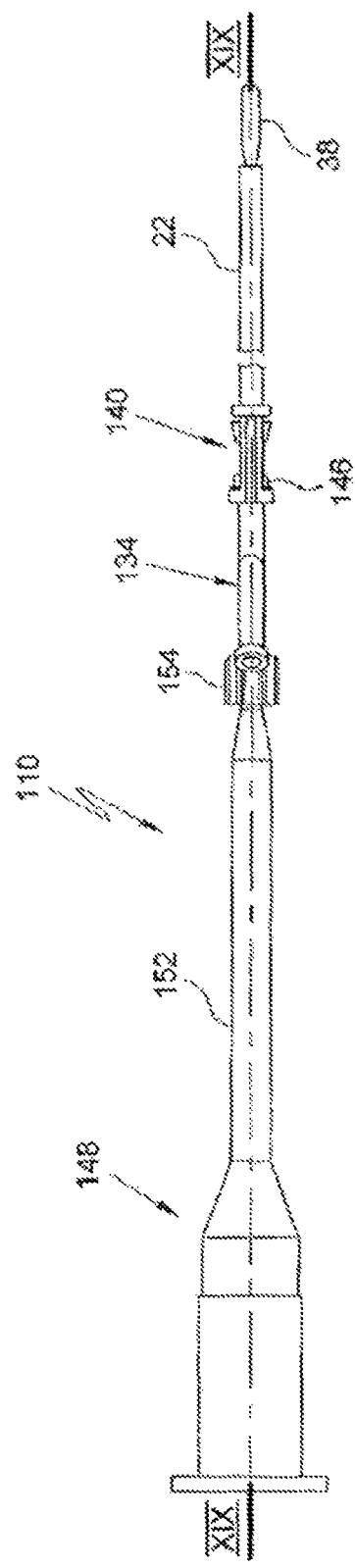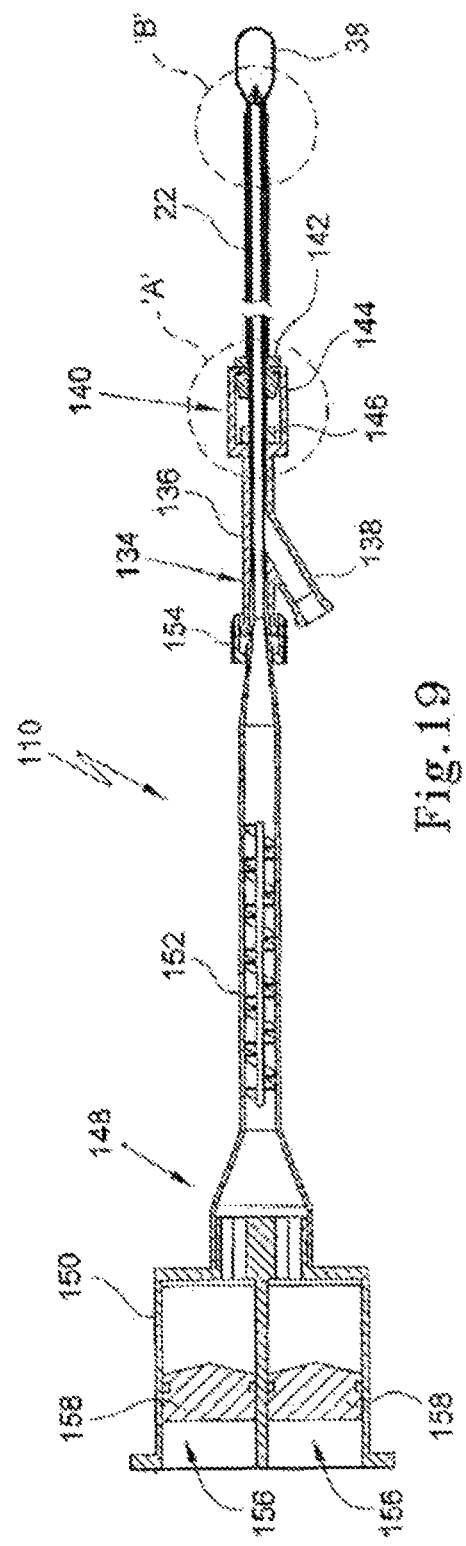

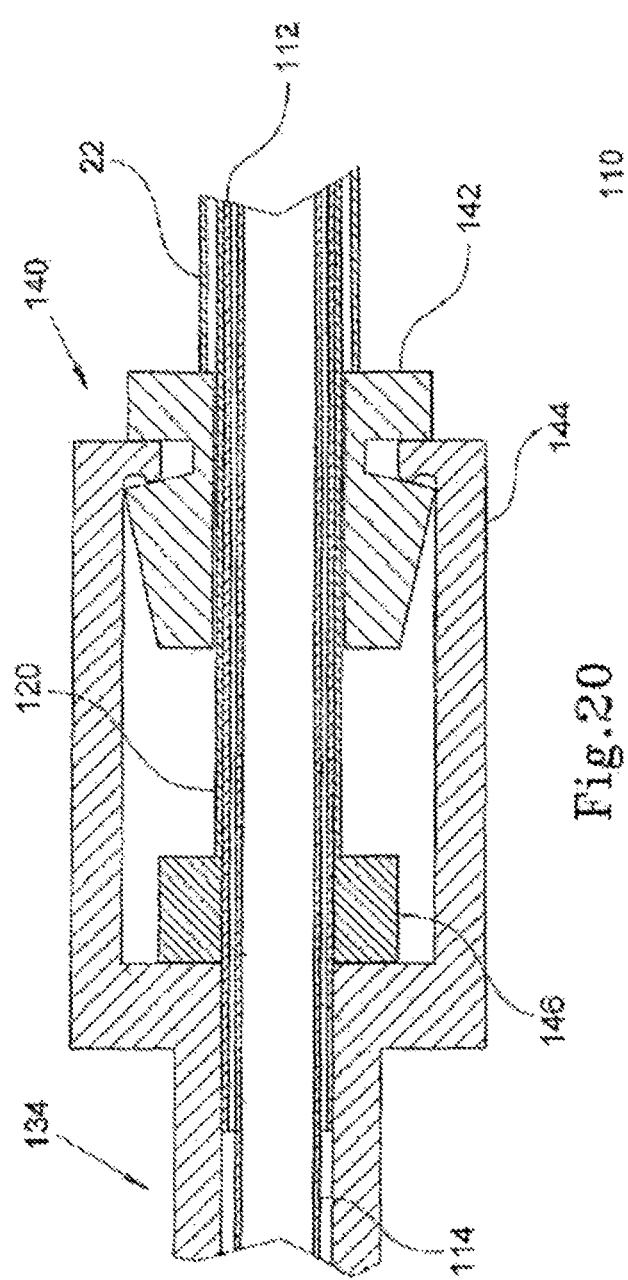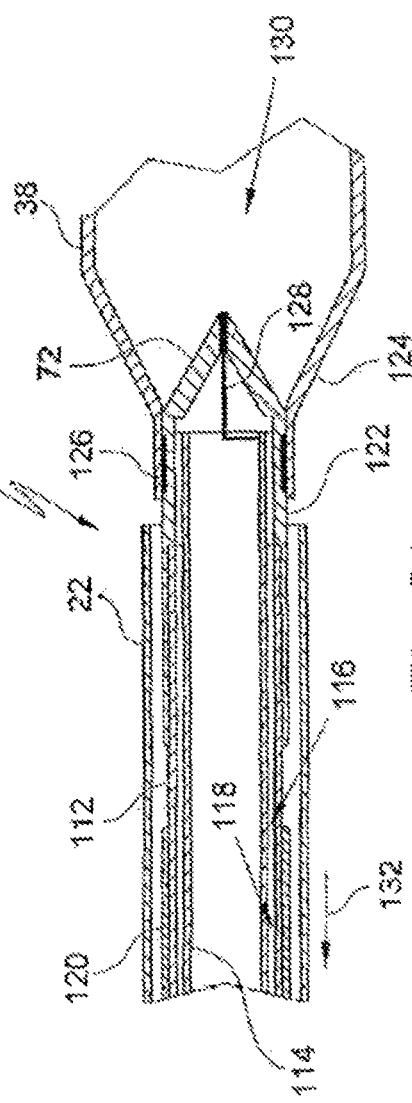

TISSUE PROSTHESIS AND METHOD OF, AND EQUIPMENT FOR, FORMING A TISSUE PROSTHESIS

CROSS-REFERENCES TO RELATED APPLICATIONS

This application is a divisional of U.S. patent application Ser. No. 12/017,430, filed on Jan. 22, 2008, now abandoned, which is a continuation of International Application No. PCT/AU2006/001176, filed on Aug. 15, 2006, which claims the benefit of U.S. Provisional Patent Application Ser. No. 60/708,670, filed on Aug. 15, 2005, the full disclosures of which are incorporated herein by reference in their entirety.

BACKGROUND OF THE INVENTION

1. Field of the Invention

This invention relates generally to the repair of tissue in a body and, more particularly, to a method of, and equipment for, forming a tissue prosthesis in situ and to a tissue prosthesis. The invention has particular, but not necessarily exclusive, application in the field of minimally invasive intervertebral disc nucleus repair.

Joints of the musculoskeletal system of the human or animal body rely on the presence of healthy cartilaginous tissue for proper operation. Cartilaginous tissue can degenerate due to a number of causes, eg. age or injury. Degradation of the tissue can reach a point where movement can cause severe discomfort and pain.

In the case of the spinal column, it comprises a series of 26 mobile vertebral bones or vertebrae connected by 75 stable articulations that control motion. The vertebrae are generally divided into posterior and anterior elements by thick pillows of bone called pedicles. The anterior element of the vertebra is a kidney shaped prism of bone with a concavity directed posteriorly and has flat superior and inferior surfaces called end plates. An intervertebral disc is sandwiched between adjacent pairs of vertebrae forming a joint between the adjacent pair of vertebrae. These discs are viscoelastic structures comprising a layer of strong deformable soft tissue. The intervertebral discs are subjected to a considerable variety of forces and moments resulting from the movements and loads of the spinal column. Each intervertebral disc has two components being the annulus fibrosis circumscribing a nucleus pulposus. The intervertebral disc cooperates with the end plates of the vertebrae between which it is sandwiched.

The primary function of the nucleus pulposus of the disc is to give the disc its elasticity and compressibility characteristics to assist in sustaining and transmitting weight. The annulus fibrosis contains and limits the expansion of the nucleus pulposus during compression and also holds together successive vertebrae, resisting tension and torsion in the spine. The end plates of the vertebrae are responsible for the influx of nutrients into the disc and the efflux of waste products from within the disc.

With age or injury, a degenerative process of the disc may occur whereby its structures undergo morphological and biological changes affecting the efficiency with which the disc operates. Thus, the nucleus pulposus may reduce in volume and dehydrate resulting in a load reduction on the nucleus pulposus, a loss in intradiscal pressure and, hence, additional loading on the annulus fibrosis. In a normally functioning disc, the intradiscal pressure generated results in deformation of the end plates of the adjacent vertebrae generating the natural pumping action which assists in the influx of the nutrients and the efflux of waste products as stated above. A drop in intradiscal pressure therefore results in less end plate deformation. The nutrients supplied to the discal tissue is reduced and metabolic wastes are not removed with the same efficiency. This contributes to a degenerative cascade.

Radial and circumferential tears, cracks and fissures may begin to appear within the annulus fibrosis. If these defects do not heal, some of the nuclear material may begin to migrate into the defects in the annulus fibrosis. Migration of the nuclear material into the annulus fibrosis may cause stretching and delamination of layers of the annulus fibrosis resulting in back pain due to stimulation of the sinu-vertebral nerve. An intervertebral disc without a competent nucleus is unable to function properly. Further, since the spine is a cooperative system of elements, altering the structure and mechanics at one location of the spinal column may significantly increase stresses experienced at adjacent locations thereby further contributing to the degenerative cascade.

In the past, operative intervention has occurred to relieve lower back pain arising from intervertebral disc degeneration. Most of this operative intervention has been by way of a discectomy where leaking nuclear material is removed or, alternatively, fusion. The primary purpose of a discectomy is to excise any disc material that is impinging on the spinal nerve causing pain or sensory changes. Fusion means eliminating a motion segment between two vertebrae by use of a bone graft and sometimes internal fixation. Biomechanical studies show that fusion alters the biomechanics of the spine and causes increased stresses to be experienced at the junction between the fused and unfused segments. This promotes degeneration and begins the degenerative cycle anew. Clearly, being an invasive operative procedure, fusion is a risky procedure with no guarantee of success.

Due to the minimal success rate of the previous two procedures, as well as their inability to restore complete function to the spinal column, alternative treatments have been sought in the form of artificial disc replacements. Theoretical advantages of artificial disc replacement over a fusion procedure include preservation or restoration of segmental motion in the spine, restoration of intervertebral architecture and foraminal height, sparing of adjacent segments of the spine from abnormal stresses and restoration of normal biomechanics across the lumbar spine. The established artificial disc replacement procedure consists of techniques that require a surgical incision on the abdomen, retraction of large blood vessels, a total excision of the anterior longitudinal ligament, anterior and posterior annulus along with the nucleus and near total removal of the lateral annulus and implantation of an articulated prosthesis. This is a major spinal column reconstruction operation.

There is therefore a need for a surgical procedure which, as far as possible, restores the biomechanics of joints such as those between adjacent vertebrae of the spine by the provision of a tissue prosthesis mimicking natural, healthy cartilaginous tissue.

BRIEF SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect of the invention, there is provided a tissue prosthesis which comprises:

an envelope of a biologically inert, elastically deformable material capable of being expanded to conform to an interior surface of a cavity formed at a site in a patient's body; and a filler material received in a fluent state in the envelope, the filler material being of the same class of material as the envelope to form, when cured, together with the envelope, a unified structure.

The envelope may be of an elastomeric material capable of expanding to up to 100 times its relaxed state. Further, the filler material may be of an elastomeric material capable of absorbing shock and withstanding compressive, tensile, bending and torsional forces. The envelope may be expanded to be stretched and retained under tension after being charged with the filler material.

In this specification, the term "expanded" and its variations is to be understood as meaning "stretched elastically".

Both the envelope and the filler material may be of an elastomeric material having a Shore Hardness in the range of between about 5 to 90 A. Preferably, the envelope and the filler material are of a silicone rubber material. However, to promote bonding between the envelope and the filler material, the envelope and the filler material may be of different grades of silicone rubber material and may be pre-treated in different ways prior to use.

The envelope may include a neck portion, the neck portion defining a zone of weakness for facilitating separation of the envelope from a delivery device. Further, the envelope may include a flow control device arranged at an inlet opening to the envelope for inhibiting back flow of the filler material from the envelope. In an embodiment, the prosthesis may include a flow control defining member, the flow control defining member being separate from the envelope and being arranged at the inlet opening to the envelope.

The envelope may carry a marker arrangement on an exterior surface for enabling the envelope to be used to assess dimensions and a shape of the cavity and positioning of the envelope in the cavity.

According to a second aspect of the invention, there is provided a tissue prosthesis which comprises:

an envelope of a foraminous, chemically inert material shaped to conform to an interior surface of a cavity formed at a site in a patient's body in which the envelope is to be placed; and a filler material received in a fluent state in the envelope, the filler material being of an elastomeric material which, prior to being cured, is urged into foramens of the envelope to form an integrated structure which inhibits relative movement between the envelope and the filler material, in use, and once the filler material has cured.

The envelope may be of a knitted biological or synthetic polymeric material. More particularly, the envelope may be of a knitted polyester material, such as polyethylene terephthalate (PET). Further, the envelope may be coated with a material of the same class as the filler material.

Once again, the envelope may include a flow control device arranged at an inlet opening to the envelope for inhibiting back flow of the filler material from the envelope. The prosthesis may include a flow control defining member, the flow control defining member being separate from the envelope and being arranged at the inlet opening to the envelope.

According to a third aspect of the invention, there is provided a method of forming a tissue prosthesis in situ at a site in a patient's body, the method comprising:

accessing the site in the patient's body;

if necessary, removing tissue from the site to form a cavity;

inserting an envelope of a biologically inert, elastically deformable material into the cavity;

charging a filler material, in a fluent state, into the envelope to cause the envelope to expand and conform to the shape of the cavity; and allowing the filler material to cure, the filler material being of the same class of material as the envelope so that, when the filler material has cured, a unified prosthesis is formed.

The method may include accessing the site by inserting an introducer through an aperture formed in tissue associated with the site and removing nuclear tissue, if required, from the site. The nuclear material may be removed by mechanical, ultrasonic, laser, Argon gas or radio frequency ablation, or the like, in combination with suction and irrigation. For example, mechanical removal may be effected by using a reaming-type tool.

Once the nuclear tissue has been removed, the method may include checking dimensions of the cavity so formed. Thus, the method may include using the envelope, containing suitable markers, to check the dimensions of the cavity. This may be effected by inflating the envelope using a suitable fluid such as a water/saline solution. Instead of using the envelope with markers, the method may include using a flexible wire fed down the introducer and checking the position of the wire using a fluoroscopic x-ray technique once the wire is in position. In yet a further way of checking the dimensions of the cavity, the method may include deploying a jacket of similar dimensions to the envelope in the cavity, inflating the jacket with the water/saline solution and, using a fluoroscope, detecting the periphery of the jacket by radio opaque markers on an outer surface of the jacket.

Once the envelope has been placed in position, the method may include checking the integrity of the envelope, i.e. to ensure that the envelope does not have any leaks or other defects. This may be effected by filling the envelope with the water/saline solution.

The method may include evacuating an interior of the envelope to inhibit the formation or entrapment of fluid bubbles in the filler material. Instead, the method may include commencing filling of the envelope from a distal end of the envelope and progressively filling the envelope towards a proximal end of the envelope (by withdrawing a filler tube or allowing the material buoyancy to lift the filler tube) to inhibit the formation or entrapment of fluid bubbles in the filler material. In the latter case, either a delivery device by which the envelope is introduced into the cavity or the envelope may define a formation allowing the escape of air as the envelope is charged with the filler material.

The method may include, once filling of the envelope has been completed and a filler element withdrawn, occluding the aperture in the tissue of the site. Occluding the aperture may comprise closing it off by a non-return valve or by crimping closed a neck portion of the envelope. A removable tube may be nested over the delivery device and may be propelled distally to remove the envelope and valve from the delivery device.

The method may include attaching the envelope to a distal end of a tubular delivery device and everting the envelope on the distal end prior to insertion of the delivery device into the introducer for delivery of the envelope into the cavity of the site.

Preferably, the method includes accessing the site percutaneously in a minimally invasive surgical procedure. Hence, the method may be used to perform minimally invasive intervertebral disc nucleus replacement and may comprise:

forming an aperture in an annulus fibrosis of the disc percutaneously;

extracting a nucleus pulposus of the disc to form a disc cavity bounded by the annulus fibrosis of the disc and end plates of vertebrae between which the disc is located;

inserting the envelope, in a relaxed state, into the cavity through the aperture;

charging the filler material into the envelope to cause the envelope to expand and conform to the shape of the disc cavity;

allowing the filler material to cure to form, together with the envelope, the unified prosthesis; and occluding the aperture.

Preferably, the method includes expanding and stretching the walls of the envelope and retaining the envelope under tension after charging it with filler material.

According to a fourth aspect of the invention, there is provided equipment for forming a tissue prosthesis in situ at a site in a patient's body, the equipment comprising:

a delivery device displaceably receivable in a lumen of an introducer, the delivery device defining a passageway;

an envelope carried at a distal end of the delivery device, the envelope being of a biologically inert, elastically deformable material capable of being expanded to conform to an interior surface of a cavity formed at the site; and a supply of a filler material chargeable in a fluent state into the envelope through the passageway of the delivery device, the filler material being of the same class of material as the envelope to form, when cured, together with the envelope, a unified prosthesis.

The equipment may include an aperture forming element to form an aperture into the site, the aperture forming element being receivable through the introducer for delivery to the site. The aperture forming element may, for example, be a trocar.

Further, the equipment may include a tissue removal mechanism insertable through the aperture for removing tissue, if required, to form the cavity. As indicated above, the tissue removal mechanism may comprise mechanical, ultrasonic, laser, Argon gas or radio frequency ablation mechanisms, or the like in combination with suction and irrigation. For example, the tissue removal mechanism may be a reaming-type tool.

The envelope may be of an elastomeric material capable of expanding to up to 100 times its relaxed state. The envelope is preferably expanded to be stretched and retained under tension after being charged with the filler material.

The envelope may include a neck portion, the neck portion defining a zone of weakness for facilitating separation of the envelope from the delivery device. Further, the envelope may includes a flow control device arranged at an inlet opening to the envelope for inhibiting back flow of the filler material from the envelope. The equipment may include a flow control defining member, the flow control defining member being separate from the envelope and being arranged at the inlet opening to the envelope.

The envelope may carry a marker arrangement on an exterior surface for enabling the envelope to be used to assess dimensions and a shape of the cavity and positioning of the envelope in the cavity.

The filler material may be of an elastomeric material capable of absorbing shock and withstanding compressive, tensile, bending and torsional forces. More particularly, the envelope and the filler material may be of an elastomeric material having a Shore Hardness in the range of about 5 to 90 A. The envelope and the filler material may be of a silicone rubber material.

The equipment may include a dispenser containing the supply of filler material.

Further, the equipment may include a sensing arrangement configured to sense a parameter of the filler material charged into the envelope. The sensing arrangement may comprise a pressure sensor for sensing the pressure of filler material charged into the envelope, a temperature sensor for sensing the temperature of the filler material charged into the envelope, be configured to sense the quantity of filler material charged into the envelope and/or comprise a flow rate sensor for sensing the rate of flow of the filler material into the envelope. Further, the sensing arrangement may be configured to sense the presence of air bubbles in the filler material charged into the envelope.

According to a fifth aspect of the invention, there is provided equipment for forming a tissue prosthesis in situ at a site in a patient's body, the equipment comprising a tubular delivery device, the delivery device defining a passageway, an envelope of the prosthesis being mountable to a distal end of the delivery device to be received in a cavity at the site;

a filler member receivable in the passageway of the delivery device, the filler member being receivable with clearance in the passageway to define a gap to enable fluid to be evacuated at least from the envelope; and a removal mechanism carried by the delivery device for enabling the envelope to be removed from the delivery device after the envelope has been charged with filler material via the filler member.

The equipment may include a tubular introducer and an aperture forming element, such as a trocar, to form an aperture at the site, the aperture forming element being receivable through the introducer for delivery to the site.

Further, the equipment may include a tissue removal mechanism insertable through the aperture for removing tissue, if required, to form the cavity.

The introducer and the delivery device may include a retaining arrangement for retaining the delivery device with respect to the introducer.

In addition the equipment may include a supply of filler material attachable to a proximal end of the filler member. The filler material may be a mixture of a plurality of parts and the supply of filler material may comprise a dispenser defining a plurality of chambers in each of which one part of the filler material is received prior to use. The dispenser may further comprise a mixer arranged intermediate an outlet of the dispenser and the proximal end of the filler member for mixing the filler material prior to charging it into the envelope.

A proximal end of the delivery device may carry a connector for connection to an evacuating mechanism such as an evacuation pump.

The equipment may include the envelope, the envelope being of an elastomeric material capable of expanding to up to 100 times its relaxed state. Preferably, the envelope is expanded to be stretched and retained under tension after being charged with the filler material. The envelope may include a neck portion, the neck portion defining a zone of weakness for facilitating separation of the envelope from the delivery device.

Further, the envelope may include a flow control device arranged at an inlet opening to the envelope for inhibiting back flow of the filler material from the envelope. The equipment may include a flow control defining member, the flow control defining member being separate from the envelope and being arranged at the inlet opening to the envelope.

A distal end of the filler member may carry an engaging member which engages the flow control device to at least partially open the flow control device and to allow the interior of the envelope to be evacuated prior to being charged with the filler material.

The envelope may carry a marker arrangement on an exterior surface for enabling the envelope to be used to assess dimensions and a shape of the cavity and positioning of the envelope in the cavity.

The filler material may be of an elastomeric material capable of absorbing shock and withstanding compressive, tensile, bending and torsional forces. The envelope and the filler material may be of an elastomeric material having a Shore Hardness in the range of about 5 to 90 A. Preferably, the envelope and the filler material are of a silicone rubber material.

The equipment may include a sensing arrangement configured to sense a parameter of the filler material charged into the envelope. The sensing arrangement may comprise a pressure sensor for sensing the pressure of filler material charged into the envelope, a temperature sensor for sensing the temperature of the filler material charged into the envelope, be configured to sense the quantity of filler material charged into the envelope and/or comprise a flow rate sensor for sensing the rate of flow of the filler material into the envelope. Further, the sensing arrangement may be configured to sense the presence of air bubbles in the filler material charged into the envelope.

According to a sixth aspect of the invention, there is provided equipment for forming a tissue prosthesis in situ at a site in a patient's body, the equipment comprising:

a tubular delivery device, the delivery device defining a passageway, an envelope of the prosthesis being mountable to a distal end of the delivery device to be received in a cavity at the site;

a stiffening element arranged to project from a distal end of the delivery device with the envelope, in use, being received over the stiffening element to be supported by the stiffening element; and a removal mechanism carried by the delivery device for enabling the envelope to be removed from the delivery device after the envelope has been charged with filler material via the filler member.

In one embodiment, the stiffening element may be an elongate element, such as a rod or tube, receivable with clearance in the passageway of the delivery device to define a gap to enable fluid to be evacuated at least from the envelope to enable fluid to be withdrawn from the envelope to collapse the envelope on to a distal end of the elongate element projecting from the distal end of the delivery device.

The equipment may include a filler member receivable in the passageway of the delivery device after removal of the stiffening element, the filler member being receivable, after removal of the stiffening element, with clearance in the passageway to define a gap to enable fluid to be evacuated at least from the envelope.

In another embodiment, the equipment may include a tubular filler member receivable in the passageway of the delivery device, the filler member being receivable with clearance in the passageway to define a gap to enable fluid to be evacuated at least from the envelope and the stiffening element being an elongate element receivable through the passage of the filler member.

BRIEF DESCRIPTION OF THE DRAWINGS

Embodiments of the invention are now described by way of example only with reference to the accompanying drawings in which:

FIG. 18 shows a plan view of another embodiment of equipment for forming a tissue prosthesis, in situ, at a site in a patient's body;

FIG. 19 shows a sectional side view taken along line XIX-XIX in FIG. 18;

FIG. 20 shows, on an enlarged scale, a sectional side view of the part of the equipment encircled by circle 'A' in FIG. 19;

FIG. 21 shows, on an enlarged scale, a sectional side view of the part of the equipment encircled by circle 'B' in FIG. 19;

DETAILED DESCRIPTION OF THE INVENTION

Figure 1:
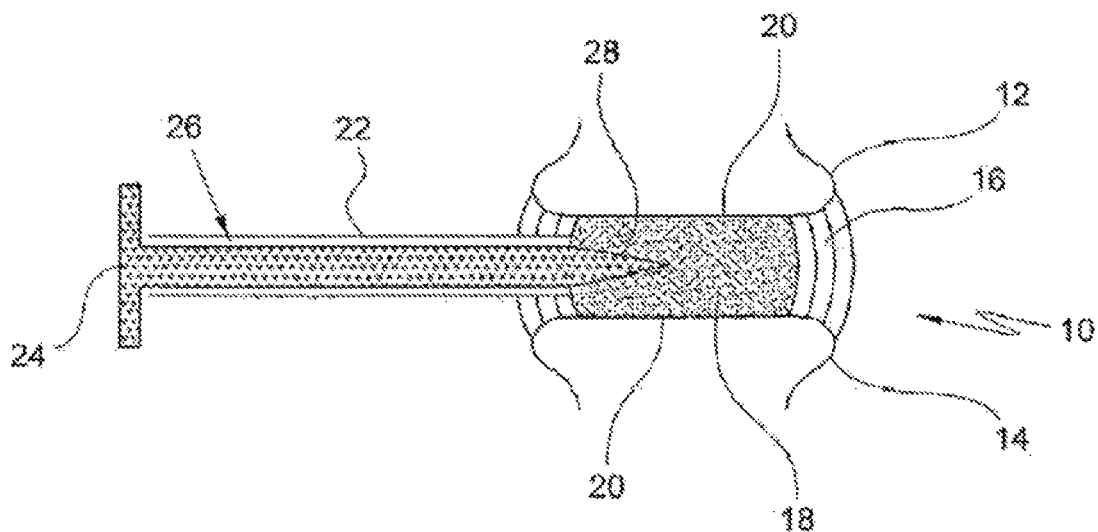
FIGS. 1-8 show schematic illustrations of various steps of a method, in accordance with an embodiment of the invention, for forming a tissue prosthesis in situ at a site in a patient's body.

While this invention has been developed specifically for the field of minimally invasive intervertebral disc nucleus replacement, it will readily be appreciated that the invention has applications in other fields requiring tissue prostheses. However, for ease of explanation, embodiments of the invention will be described below with reference to minimally invasive intervertebral disc nucleus replacement.

An intervertebral disc 10 is arranged between adjacent vertebrae 12 and 14. The disc 10 comprises an annulus fibrosis 16 made up of concentric layers of fibrous tissue. The annulus fibrosis 16 circumscribes a nucleus pulposus 18 of the disc 10, the nucleus pulposus 18 being of soft tissue. The disc 10 is sandwiched between end plates 20 of the vertebrae 12 and 14. Relative movement between the vertebrae 12 and 14 causes compression of the nucleus pulposus 18 by the end plates 20. This serves to assist in the influx of nutrients into the disc 10 and the efflux of waste products from within the disc 10.

Figure 2:
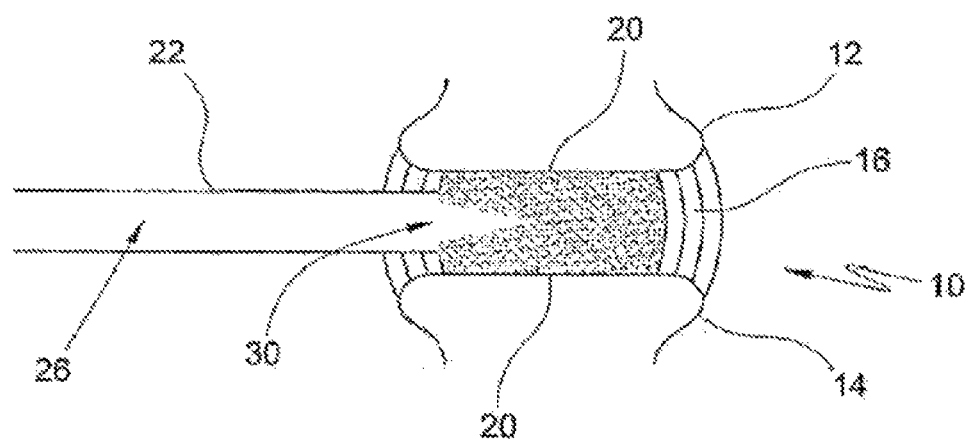
Figure 3:
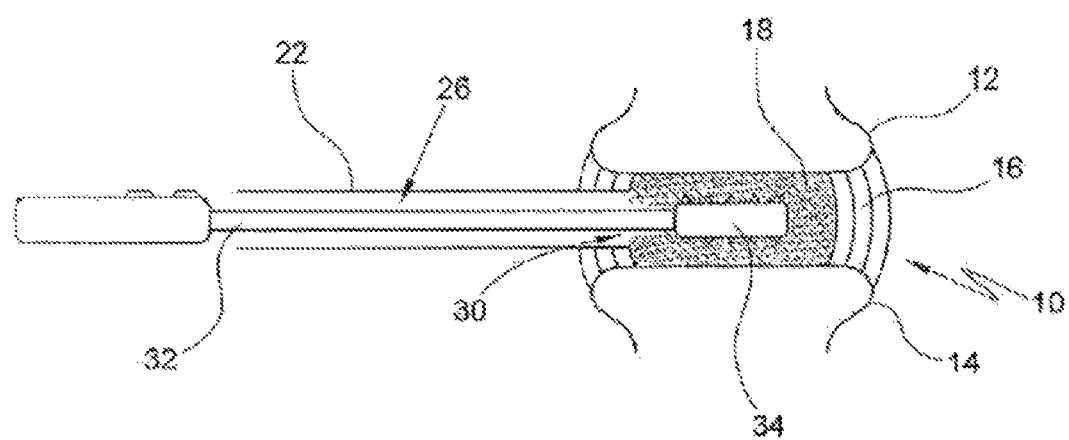

In a method of forming a tissue prosthesis, in situ, in accordance with an embodiment of the invention, a damaged nucleus pulposus 18 of the disc 10 is removed and is replaced by an artificial prosthesis. Thus, in an initial step as shown in FIG. 1 of the drawings, an introducer 22 is inserted percutaneously into abutment with the disc 10. An aperture forming element in the form of a trocar 24 is inserted into a lumen 26 of the introducer 22. A point 28 of the trocar pierces the annulus fibrosis 16 of the disc 10 forming an aperture 30 (FIG. 2) in the annulus fibrosis 16 of the disc 10.

Figure 4:
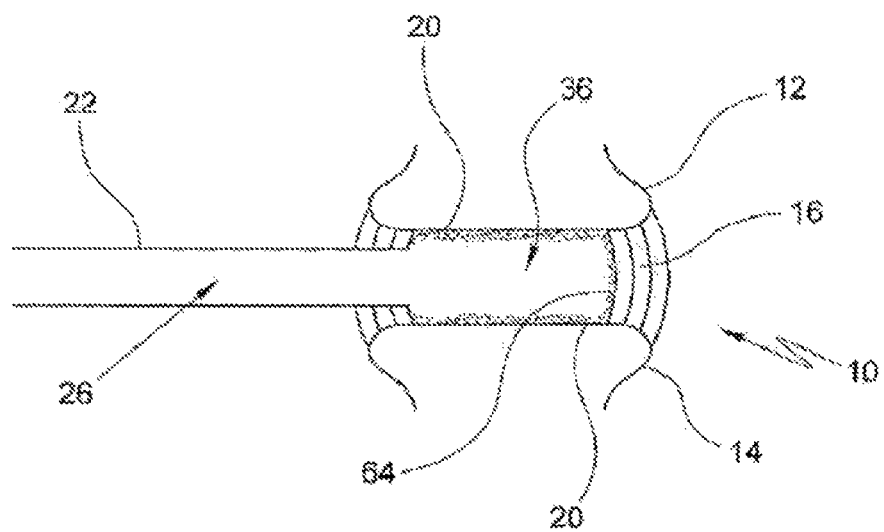
Figure 5:
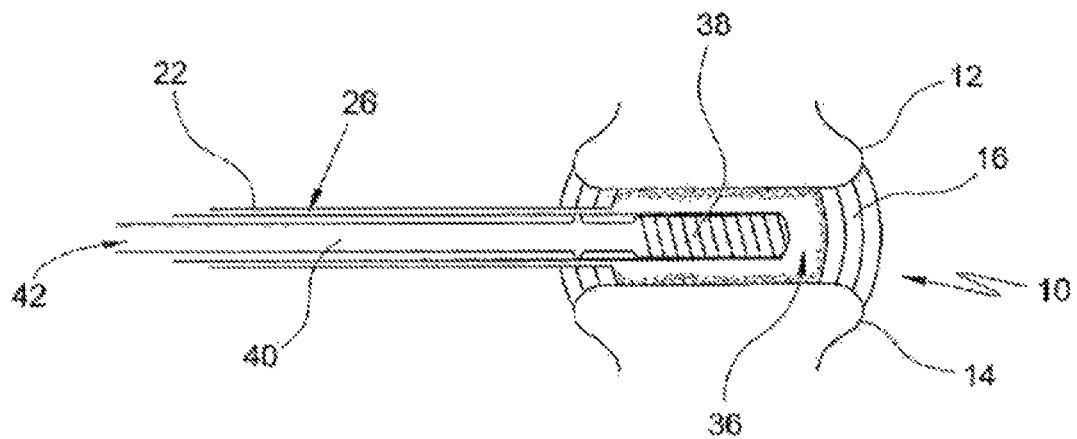
Figure 6:
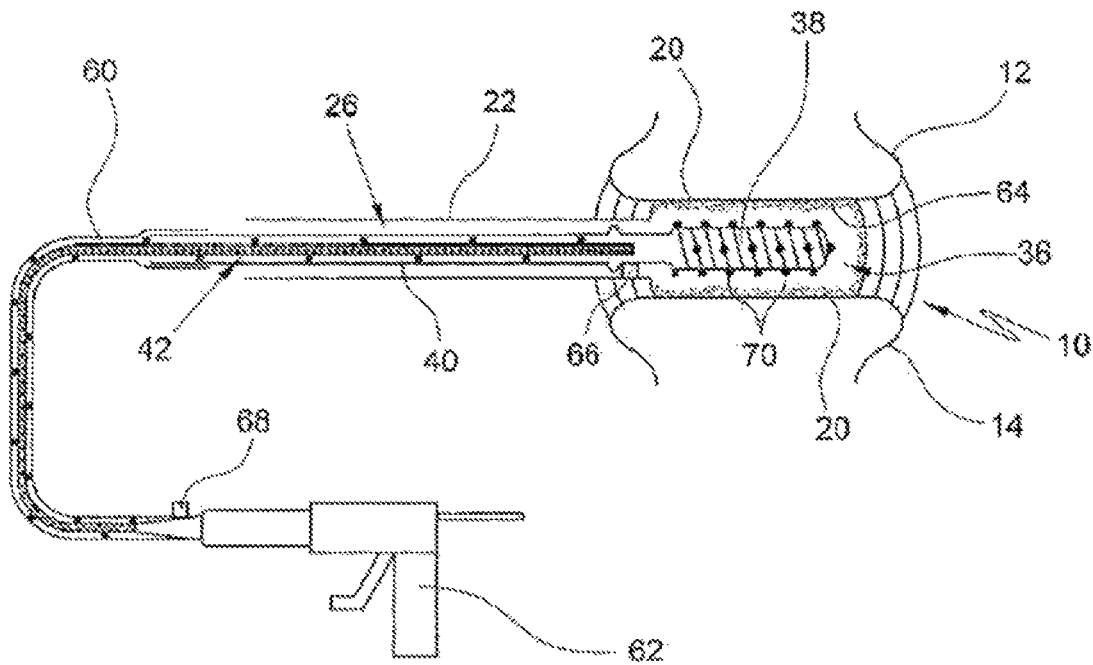

After the formation of the aperture 30 the trocar 24 is removed from the introducer 22. Once the trocar 24 has been removed, a nucleotomy is performed on the disc 10. The nucleotomy involves the removal of nuclear tissue constituting the nucleus pulposus 18. While various methods of removing the nucleus pulposus can be used, the example shows the use of a mechanical device 32. The mechanical device 32 comprises a reaming tool 34. The mechanical device 32 is inserted through the lumen 26 of the introducer and the aperture 30 in the annulus fibrosis 16 of the disc 10 into the nucleus pulposus 18. The reaming tool 34 is operated to remove the nucleus pulposus as shown in FIG. 4 of the drawings so that a cavity 36 remains. The cavity 36 is bounded by the annulus fibrosis 16 and the end plates 20 of the vertebrae 12 and 14. Residue 64 of the nucleus pulposus 18 remains resulting in the cavity 36 having irregular walls.

An envelope 38 of an elastomeric material, more particularly, a silicone rubber material is mounted on a distal end of a tubular delivery device 40. The tubular delivery device 40 defines a passageway 42. The envelope 38 is made from the silicone rubber material which is biologically inert and which can elastically deform up to 100 times the size of the envelope 38 in its relaxed state.

Figure 10:
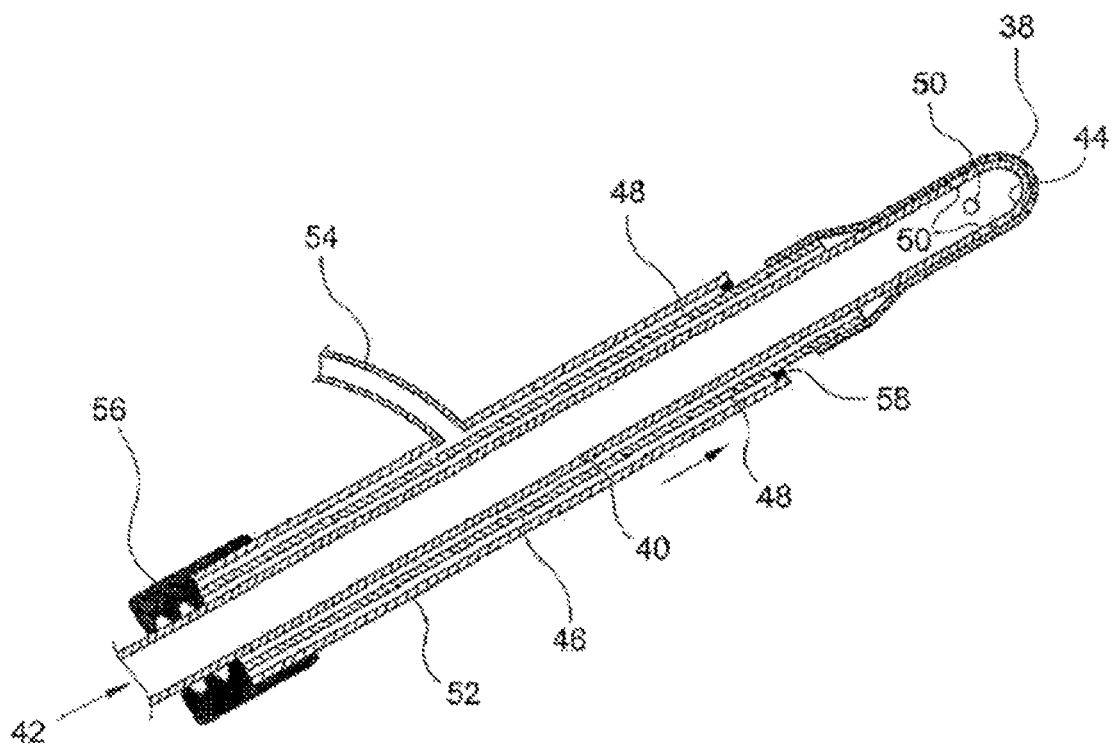
FIG. 10 shows a schematic, sectional side view of part of equipment, in accordance with another embodiment of the invention, for forming a tissue prosthesis, in situ at a site in a patient's body.

In one embodiment, as shown in greater detail in FIG. 10 of the drawings, the envelope 38, in its relaxed, or deflated, state, is a snug fit over a distal end 44 of the delivery device 40. A first sleeve 46 is arranged coaxially over the delivery device 40 adjacent the distal end 44 of the delivery device 40. This sleeve 46 has a plurality of openings 48 defined in it. These openings 48 cooperate with openings 50 at the distal end 44 of the delivery device 40. A further sleeve 52 is mounted coaxially about the sleeve 46 and communicates with an evacuation device (not shown) via an evacuating tube 54. Proximal ends of the sleeves 46 and 52 are sealed against an outer surface of the delivery device 40 via seals 56. A further seal 58 is arranged between a distal end of the sleeve 52 and the sleeve 46.

When filler material, referenced generally by the reference numeral 60, is injected into the envelope 38, a low pressure is, simultaneously or prior to injection, imparted to the distal end of the delivery device 40 to evacuate fluid, more particularly, air, from within the envelope 38. This assists in airless mixing and ensures that the formation of air bubbles in the filler material 60 is inhibited. Evacuation of air also inhibits entrapment of air within the envelope 38 by the incoming filler material 60 and facilitates the flow of the filler material 60 into the envelope 38. As the filler material 60 is charged into the envelope 38 through the filling openings 50, air is drawn out of the envelope 38 by operation of the evacuation device via the evacuation tube 54. The air is received between the outer surface of the delivery device 40 and the sleeve 46. This air passes through the openings 48 in the sleeve 46 and through the evacuation tube 54.

The filler material 60 is also of a silicone rubber material which is able to absorb shocks and withstand compressive, tensile, bending and torsional forces imparted to it by movement of the vertebrae 12 and 14. In addition, due to the fact that the filler material 60 is the same class or type as the material of the envelope 38, once the filler material has cured in the envelope 38, a unified or single, integrated structure is formed which is resistant to delamination and relative movement between the envelope 38 and the filler material 60.

The envelope 38 is made from a silicone rubber material having the following characteristics:

a Shore hardness (A scale) in the range from about 20-50;
a tensile strength in the range from about 2700 kPa to 11000 kPa;
an elongation of between about 400% and 800%; and
a tear strength of between about 1700 kg/m and 4500 kg/m.

The filler material 60 is also of a silicone rubber material which, prior to use, is stored in two separate parts. The filler material 60, comprising the combined parts, when mixed in a ratio of 1:1 and cured, has the following characteristics:

a Shore hardness (A scale) in the range from about 20 to 40, more particularly, about 25 to 30 and, optimally, about 28;
a tensile strength in the range form about 7000 kPa to about 9500 kPa, more particularly, about 8000 kPa to about 9000 kPa and, optimally, about 8500 kPa;
an elongation in the range from about 550% to 700%, more particularly, about 600% to 650% and optimally, about 640%; and
a tear strength in the range from about 1000 to 2000 kg/m, more particularly, about 1250 kg/m to 1750 kg/m and, optimally, about 1500 kg/m.

One example of a suitable material for the filler material has the following characteristics after mixing the parts in a 1:1 ratio and after curing:

a Shore hardness (A scale) of 28;
a tensile strength of 8439 kPa;
an elongation of 639%; and
a tear strength of 1500 kg/m.

The filler material 60 is treated to contain 5%, by volume, barium sulphate to appear radio-opaque under X-ray, CT, fluoroscopy and MRI. In addition, the filler material 60 contains a catalyst and has a scorch time of between about 1.5 to 2.5 minutes with a curing time of about 5 minutes. When the filler material 60 is charged into the envelope 38 it causes inflation or expansion of the envelope 38 in an elastically deformable manner. Expansion of the envelope 38 can occur to such an extent that, where necessary, the expanded envelope 38 distracts the vertebrae 12 and 14 to restore the original spacing between the vertebrae 12 and 14. By using radio-opacity in the filler material 60, distraction of the vertebrae 12 and 14 can be monitored in real time using a fluoroscope or the similar equipment.

Further, the envelope 38 conforms to the shape of the cavity 36. Because the envelope 38 expands within the cavity 36 and conforms closely to the shape of the cavity 36, the envelope 38 self anchors within the cavity 36 and "extrusion" of a unified prosthesis 100, comprising the envelope 38 and the filler material 60, formed through the aperture 30 previously formed in the annulus 16 of the disc is inhibited.

The material for the envelope may, depending on the grade or class of material used, be post cured for a period of time. This is effected by placing the moulded envelope 38 into an oven, for example, for a period of about 1 to 4 hours at a temperature of about 150.degree. C. to 180.degree. C.

By having the material of the envelope 38 and the filler material 60 of the same type, but different grades or classes, chemical bonding between the materials is enhanced which encourages the formation of the prosthesis 100.

The filler material 60 is dispensed from a dispensing source such as a dispenser 62.

As described above, when the nucleus pulposus 18 has been removed, a residue 64 remains about the inner surface of the annulus fibrosis and on the end plates 20 of the vertebrae 12 and 14. This residue 64 is of an irregular shape. Therefore, in charging the envelope 38 with the filler material 60, it is necessary to monitor the charging of the filler material 60 into the envelope 38. This is done by a sensing arrangement. In one embodiment of the invention, the sensing arrangement comprises a pressure sensor 66 at an inlet to the envelope 38. In another embodiment, the sensing arrangement comprises a volume sensor 68 arranged at an outlet of the dispenser 62 for monitoring the volume of filler material 60 dispensed. The sensing arrangement could, in addition or instead, be a flow rate sensor which monitors the rate of flow of the filler material 60.

Yet a further method of monitoring filling of the envelope 38 is monitoring back flow of filler material 60 from between the envelope 38 and the distal end of the delivery device 40. As the filler material 60 oozes out it may loosen the envelope 38 allowing the delivery device 40 to be removed.

It is also necessary to monitor the shape and size of the cavity 36 taking the residue 64 into account. This can be achieved in a number of ways. One of the ways in which this can be achieved is by having radio opaque markers 70 arranged on the envelope 38. Prior to charging the envelope 38 with the filler material 60, the envelope 38 can be expanded to conform to the shape of the cavity 36 by means of a water/saline solution or a radio opaque solution. The markers 70, being radio opaque, are monitored under a fluoroscope to determine the shape and size of the cavity 36.

Other methods of assessing the size of the cavity 36 include the use of a flexible wire inserted down the lumen 26 of the introducer 22, the wire being monitored by a fluoroscope. Yet a further way of monitoring the shape and size of the cavity 36 is by use of a dedicated jacket, of similar dimensions to the cavity 36, which is inserted into the cavity 36 and inflated using the water/saline solution or the radio opaque solution. The jacket carries radio opaque markers which are monitored by a fluoroscope.

Figure 7:
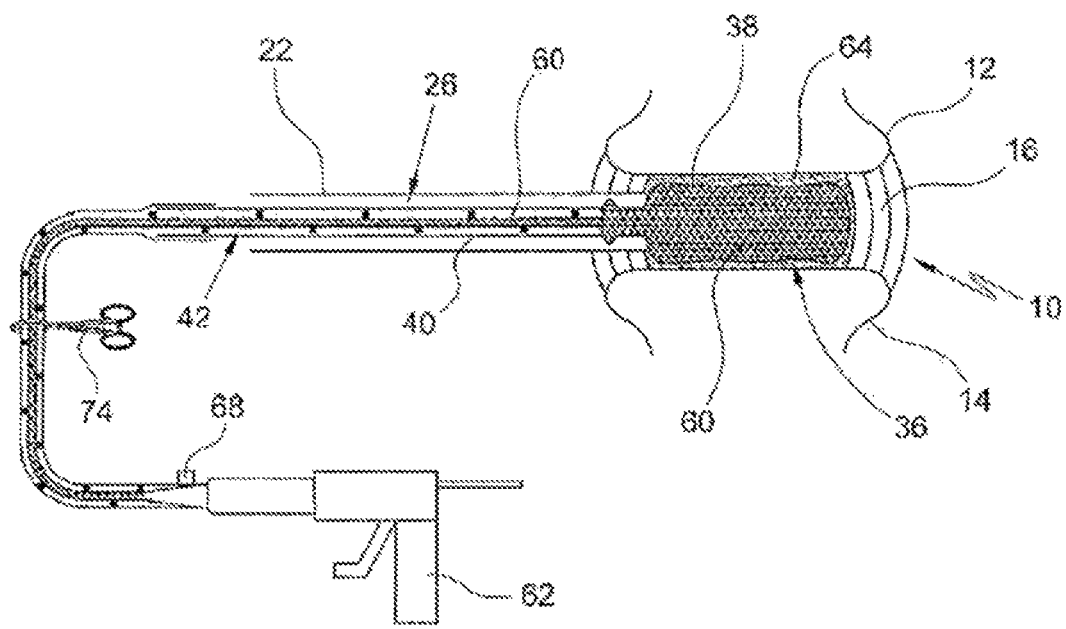

After the shape and size of the cavity 36 have been determined, the filler material 60 is dispensed from the dispenser 62 and is monitored via the sensing arrangements 66 or 68, as the case may be. As illustrated in FIG. 7 of the drawings, the filler material 60 causes elastic expansion or inflation of the envelope 38 so that the envelope 38 conforms to the shape of the cavity 36 and bears against the residue 64 of the nucleus pulposus remaining in the cavity 36. The envelope 38, having been elastically expanded by the filler material 60, remains under tension around the filler material 60 while conforming to the shape of the cavity 36.

Figure 13:
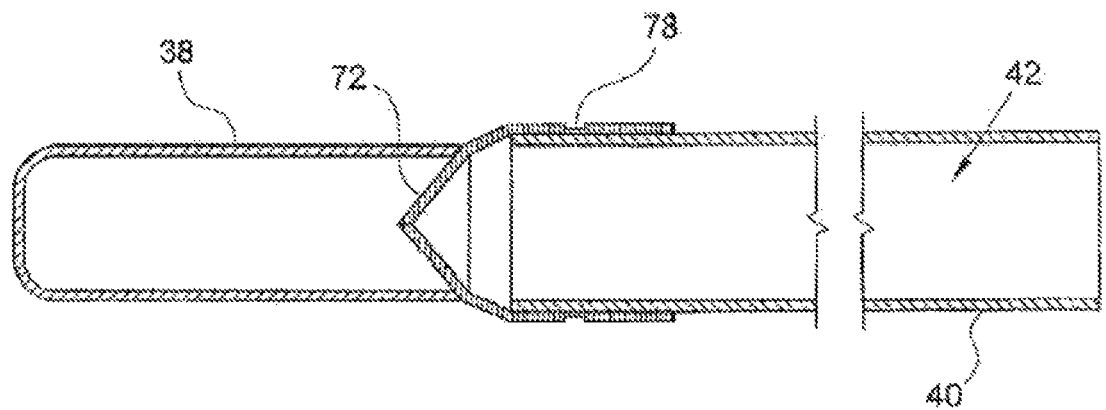
FIG. 13 shows a sectional side view of an envelope, attached to a delivery device, the envelope forming part of a tissue prosthesis, in accordance with yet a further embodiment of the invention.

Backflow filler material 60 from the interior of the envelope 38 is controlled either by a valve 72 as shown in FIG. 13 of the drawings or by a clamping device 74 as shown in FIG. 7 of the drawings. The valve 72 is a duckbill valve and acts as a one way valve so that backflow of filler material 60 from the envelope 38 is inhibited.

Figure 8:
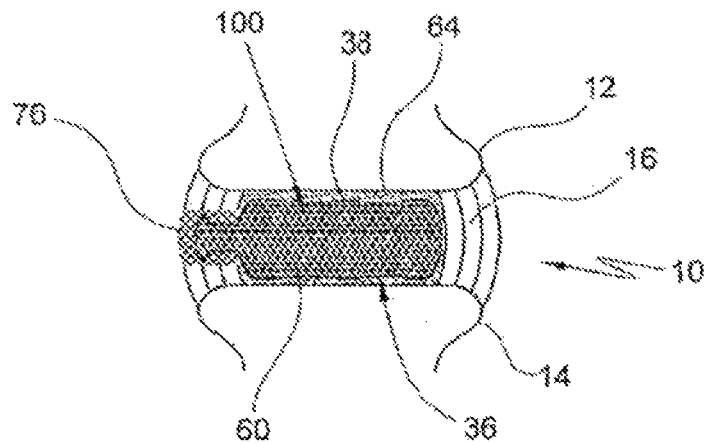

Once the envelope 38 has been filled and has expanded so that it conforms closely to the shape of the cavity 36 and is received snugly in the cavity 36, the filler material 60 is allowed to cure for a predetermined period of time of, for example, about 10 minutes. After curing of the filler material 60, the delivery device 40 is removed leaving the aperture 30 occluded as shown at 76 in FIG. 8 of the drawings. The unified tissue prosthesis 100 so formed is fully cured after about 24 hours.

To facilitate removal of the delivery device 40 from the envelope 38, the envelope 38 has a zone of weakness in the form of a circumferential groove 78 (FIG. 14) formed at a proximal end. As the delivery device 40 is withdrawn, when its distal end comes into register with the groove 78, the delivery device 40 is twisted relative to the envelope to cause a break at the groove 78 to form the occlusion 76 in the aperture 30 of the annulus fibrosis 16 of the disc 10.

Figure 9:
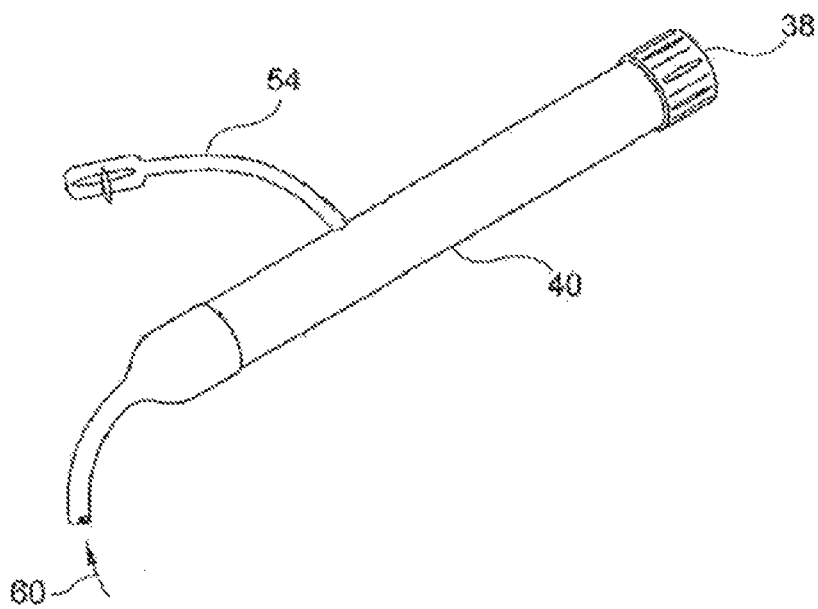
FIG. 9 shows a schematic illustration of a delivery device for use in the method.
Figure 12:
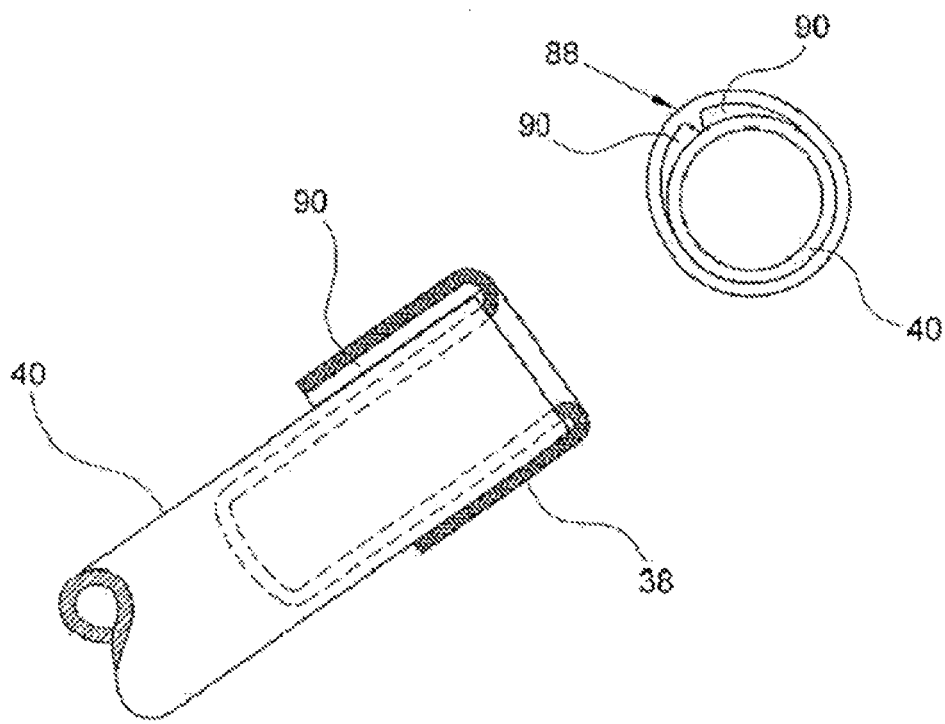
FIG. 12 shows a schematic, side view and end view of part of the equipment.
Figure 14:
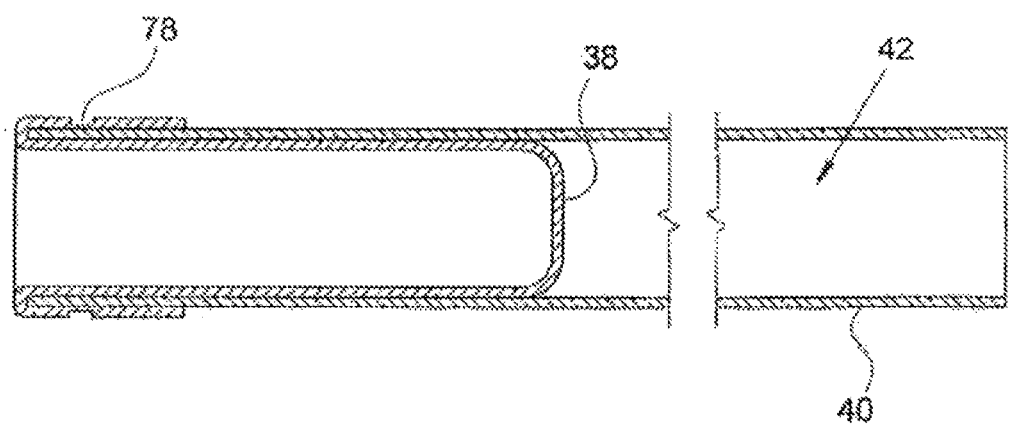
FIG. 14 shows a sectional side view of another mounting of the envelope on the delivery device.

FIG. 12 shows another way of delivering the envelope 38 into the cavity 36. In this embodiment of the invention, the envelope 38 is everted to lie within the distal end of the delivery device 40 to facilitate its insertion into the cavity 36. A similar arrangement is shown in FIG. 9 and FIG. 14 of the drawings.

Figure 11:
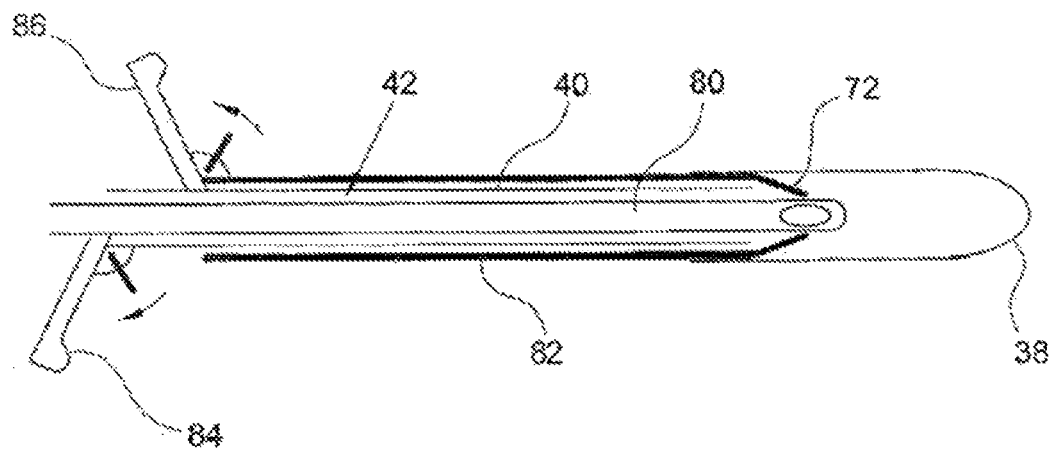
FIG. 11 shows a schematic, sectional side view of another embodiment of the equipment.

In FIG. 11 of the drawings, another embodiment of equipment for forming the tissue prosthesis 100 is shown. In this embodiment, a filler tube 80 is used. The tube 80 is received in the passageway 42 of the delivery device 40. A sleeve 82 is arranged coaxially about the delivery device 40. A first displacement device, such as a trigger, 84 is provided for controlling relative movement between the delivery device 40 and the tube 80. A second displacement device, which may also be in the form of a trigger, 86 controls relative movement between the delivery device 40 and the sleeve 82.

The equipment, as shown in FIG. 11 of the drawings, is for use where an evacuating device is not used. Thus, to fill the envelope 38, the tube 80 is urged towards the distal end of the envelope 38 and charging of the filler material 60 into the envelope 38 commences at the distal end of the envelope 38. Filling of the envelope 38 progresses from its distal end towards its proximal end. Thus, as filler material 60 is charged into the envelope 38, the tube 80 is slid proximally relative to the tube 40 by manipulating the trigger 84 or slides back through buoyancy of the filler material. Once the envelope 38 is in its fully inflated state, the envelope 38 is urged off the distal end of the delivery device 40 by manipulating the trigger 86. As the tube 80 is withdrawn from the valve 72 and the envelope 38 is removed from the distal end of the delivery device 40, the valve 72 closes to form the occlusion 76.

To facilitate expulsion of air when an evacuating system is not being used, the envelope 38 has a bead 88 (FIG. 12) formed along that portion which seats on the distal end of the delivery device 40 to create passages 90 through which air can be discharged as the envelope 38 is charged with the filler material 60.

As described above, the envelope 38 is of a silicone rubber material which can be inflated up to 100 times its relaxed size without rupturing. In another embodiment, the envelope 38 is of a less expansible material such as a biological or a synthetic polymeric material. A suitable synthetic polymeric material may, for example, be a polyester such as polyethylene terephthalate (PET). The envelope 38 is of a knitted PET material so that, when the filler material 60 is charged into the envelope 38, the filler material fills foramens or interstices in the envelope 38 to form an integrated structure which resists relative movement between the filler material 60 and the envelope 38. Alternatively, the knitted PET material may be coated with silicone allowing the filler material 60 to integrate with the coating.

Figure 15:
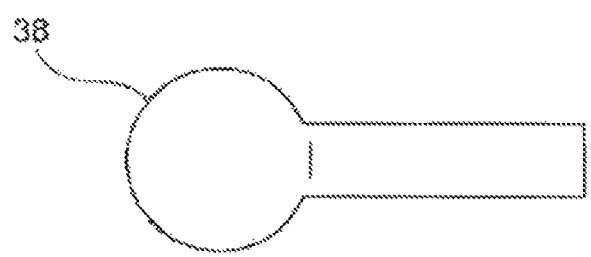
FIGS. 15-17 show different shapes of envelopes for use in the tissue prosthesis.
Figure 16:
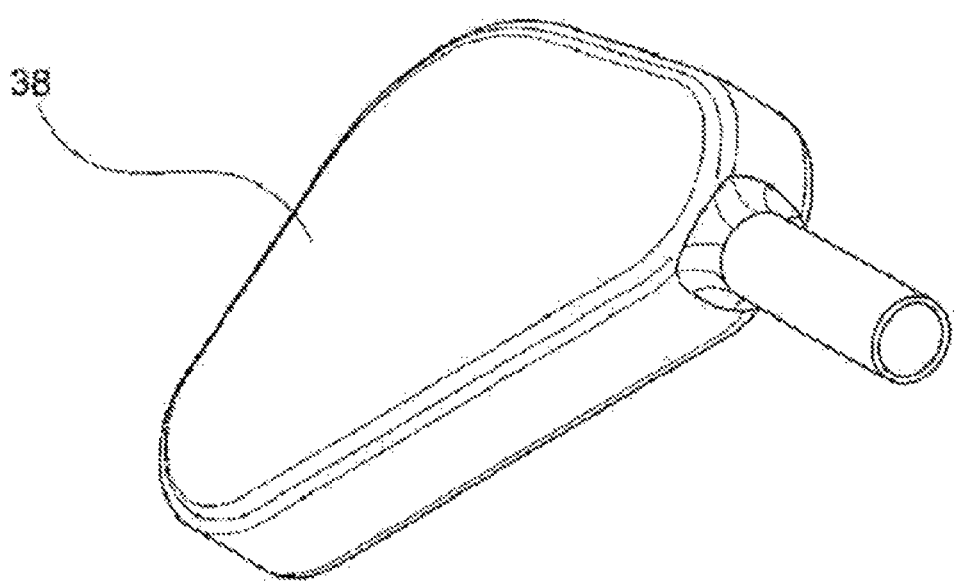
Figure 17:
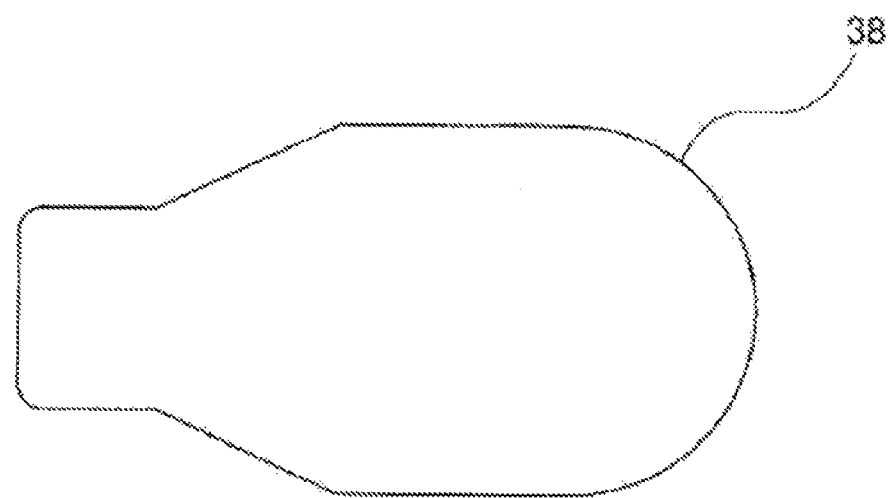

FIGS. 15 to 17 show different shapes of envelopes 38 which can be used depending on which intervertebral disc 10 is to have its nucleus pulposus 18 replaced.

Referring now to FIGS. 18 to 21 of the drawings, yet a further embodiment of equipment for forming a tissue prosthesis, in situ, at a site in a patient's body is illustrated. With reference to the previous drawings, like reference numerals refer to like parts, unless otherwise specified.

In this embodiment, the equipment 110 comprises a delivery device in the form of an envelope tube 112. The envelope tube 112 carries the envelope 38 at its distal end.

A filler member in the form of a filler tube 114 is slidably received within a passage 116 of the envelope tube 112. As illustrated more clearly in FIG. 21 of the drawings, the filler tube 114 has a smaller outer diameter than an inner diameter of the envelope tube 112 to form an annular gap 118 between the filler tube 114 and the envelope tube 112.

A removal mechanism in the form of a push-off tube 120 is a snug fit on the outer surface of the envelope tube 112.

In this embodiment, the envelope 38 is of a two part construction comprising a sleeve 122 (FIG. 21) to which an envelope defining member 124 is adhesively bonded as shown by an annular adhesive layer 126. The sleeve 122 defines the valve 72.

A distal end of the filler tube 114 carries an engaging member 128 which engages and opens the valve 72 so that the annular gap 118 is in flow communication with an interior 130 of the envelope 38. A distal end of the push-off tube 120 terminates short of a proximal end of the sleeve 122 of the envelope 38. However, it is also to be noted, as will be described in greater detail below, that the envelope tube 112 is displaceable relative to the push-off tube 120 in the direction of arrow 132.

Instead of the engaging member 128, the valve 72 could have a small opening (not shown) in it. The size of the opening in the valve 72 is selected to allow the passage of air through it but is sufficiently small that the viscosity of the filler material will inhibit the passage of the filler material through it.

Yet a further way of evacuating the interior 130 of the envelope 38 is to insert the filler tube 112 into the interior 130 of the envelope 38 and to have a slit (not shown) in the filler tube 114 upstream of the valve 72. Thus, if the valve 72 seals about the filler tube 112, air can still be drawn from the interior 130 of the envelope 38 into the gap 116 via the slit when the evacuation device is operated.

A proximal end of the envelope tube 112 carries a connector 134. The connector 134 is a Y-connector having a primary member 136 and a secondary member 138 projecting from the primary member 136. The envelope tube 112 is fast with the primary member 136 of the connector 134. The secondary member 138 of the connector 134 is in flow communication with the passage 116 of the envelope tube 112 and, hence, in use with the gap 118 between the envelope tube 112 and the filler tube 114. The secondary member 138 is connectable to an evacuation device (not shown) such as an evacuation pump for creating a low pressure in the gap 118 and, via the engaging member 128 opening the valve 72, the interior 130 of the envelope 38 prior to filler material being charged into the interior 130 of the envelope 38.

As shown more clearly in FIG. 20 of the drawings, the connector 134 includes a retaining mechanism 140 for retaining the envelope tube 112 in position relative to the introducer 22. The retaining mechanism 140 comprises a receiving formation 142 carried at a proximal end of the introducer 22. The retaining mechanism 140 further includes a clip portion 144 forming the distal end of the connector 134 which clips into the receiving formation 142 to retain the envelope tube 112 in position relative to the introducer 22.

A proximal end of the push-off tube 120 carries a gripping formation 146 which is accessible externally of the retaining mechanism 140 for enabling the push-off tube 120 to be held while the envelope tube 112 is moved in the direction of the arrow 132 after charging of the envelope 38 with the filler material.

The equipment 110 further includes a dispensing device 148 for dispensing filler material. The dispensing device 148 includes a dispenser 150 feeding into a mixing device in the form of a static mixer 152. A distal end of the static mixer 152 carries the filler tube 114. A Luer lock arrangement 154 is arranged at the distal end of the static mixer 152 and connects the dispensing arrangement 148 to the connector 134.

The filler material is of a silicone rubber, as indicated above. To inhibit curing of the filler material prior to its being charged into the envelope 38, the filler material is retained in two, separate parts. Thus, the dispenser 150 includes two reservoirs 156 in each of which a part of the filler material is initially received. Each reservoir 156 has a plunger 158 associated with it for dispensing the parts from the reservoirs 156 into the static mixer 152 where the parts are mixed prior to being charged into the envelope 38. It is to be noted that the plungers 158 are displaceable together with each other via a suitable displacing device (not shown) such as a pneumatic gun.

Thus, in use, the filler material to be charged into the envelope 38 is provided in the dispensing arrangement 148. The dispensing arrangement 148 is connected to the connector 134 via the Luer lock 154. An envelope 38, in a deflated condition, is mounted on the envelope tube 112. After the nucleotomy has been performed on the disc 10, the envelope tube 112 with the envelope 38 on its distal end is inserted through the introducer 22 so that the envelope 38, in its deflated condition, is received within the cavity 36 of the disc 10. The filler tube 114 is inserted into the interior of the filler tube 112 so that the engaging member 128 engages the valve 72 and opens the valve 72. By opening the valve 72, the interior 130 of the envelope 38 is placed in fluid communication with the gap 118 between the envelope tube 112 and the filler tube 114.

An evacuation device (not shown) is attached to the secondary member 138 of the connector 134 and a vacuum is drawn. This creates a low pressure within the gap 118 and the interior 130 of the envelope 38 and inhibits the formation of air bubbles in the prosthesis 100 as the filler material is charged into the envelope 38.

The filler material is dispensed from the dispensing device 148 into the filler tube 114 and into the interior 130 of the envelope 38. This causes the envelope 38 to expand elastically to conform to the shape of the cavity 36 of the disc 10 with the envelope 38 being retained under tension by the filler material.

After charging of the filler material into the interior 130 of the envelope 38, the filler tube 114 is withdrawn. Withdrawal of the filler tube 114 causes withdrawal of the engaging member 128 allowing the valve 72 to close to inhibit leakage of filler material from the interior 130 of the envelope 38.

After curing, the envelope tube 112 is moved relative to the push off tube 120 in the direction of the arrow 132 by holding the push off tube 120 using the gripping device 146. This urges the sleeve 122 of the envelope 38 off the end of the envelope tube 112 as the envelope tube 112 is withdrawn relative to the push off tube 120. The valve 72 occludes the opening to the envelope 38 and the aperture 30 previously formed in the annulus fibrosis 16 of the disc 10. The equipment 110, including the introducer 22, is then withdrawn from the patient's body and the procedure is complete.

Figure 22:
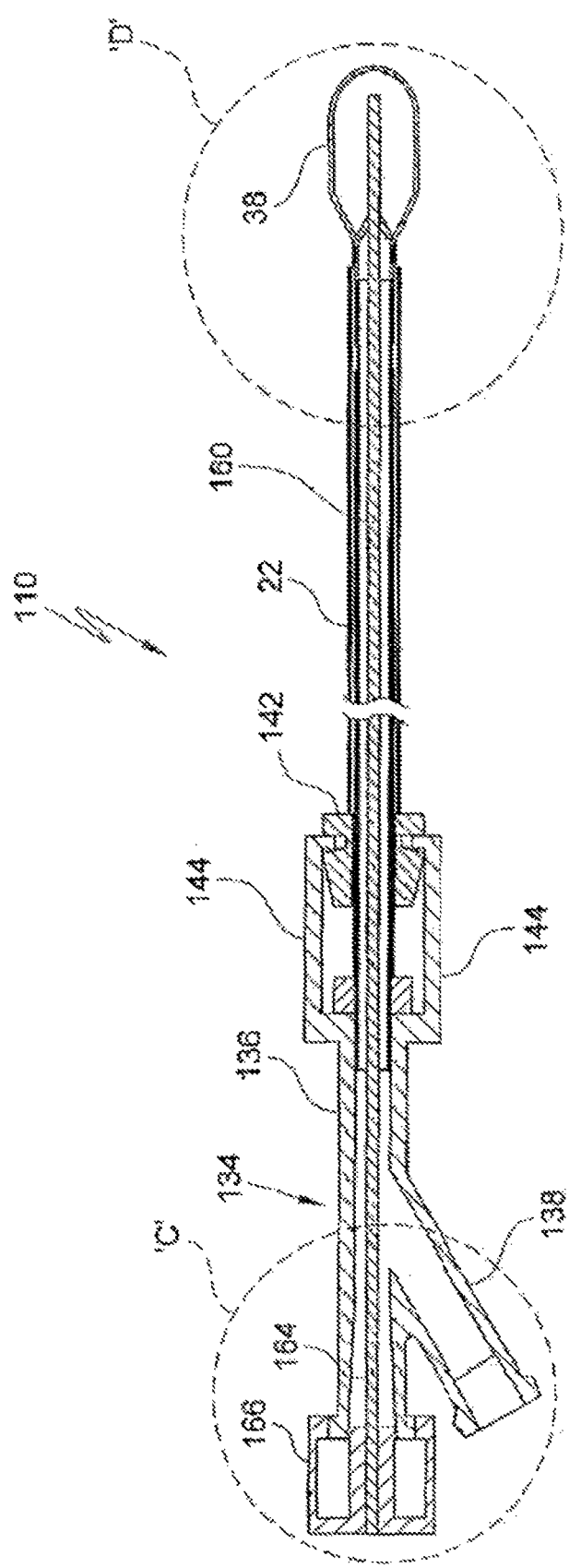
FIG. 22 shows a sectional side view of yet a further embodiment of equipment for forming a tissue prosthesis, in situ, at a site in a patient's body.
Figure 23:
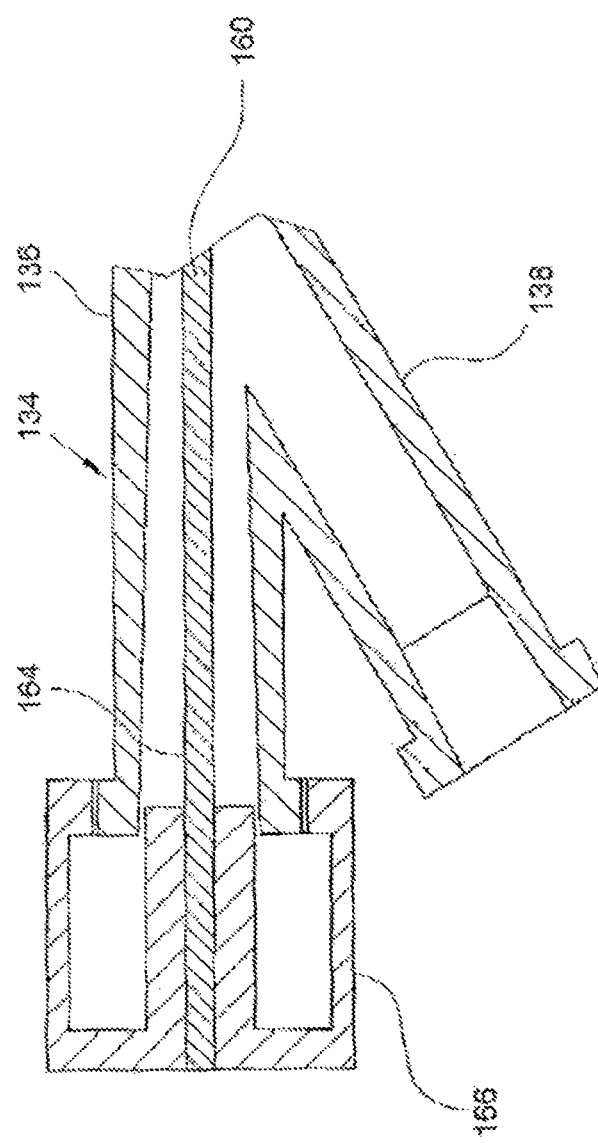
FIG. 23 shows on an enlarged scale, a sectional side view of the part of the equipment encircled by circle 'C' in FIG. 22.
Figure 24:
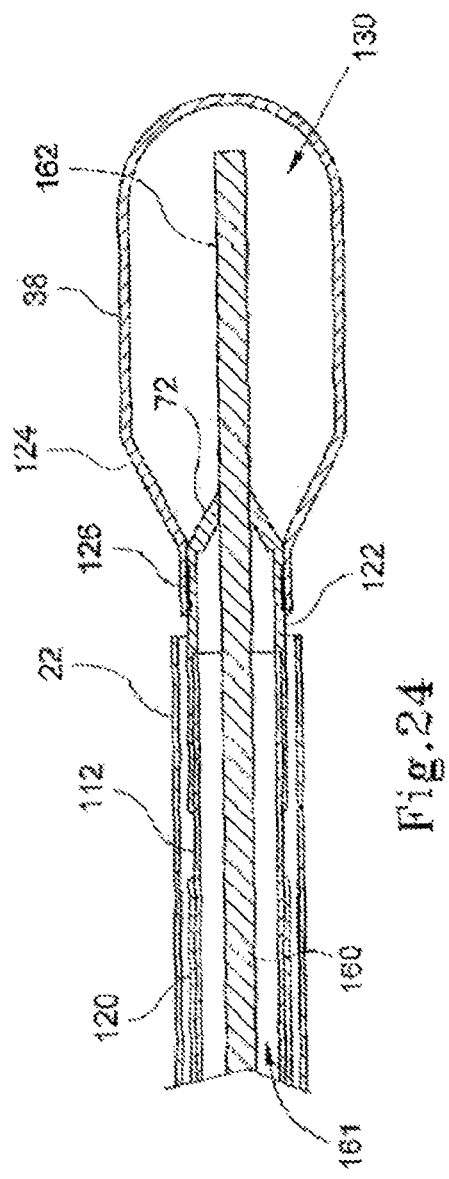
FIG. 24 shows on an enlarged scale, a sectional side view of the part of the equipment encircled by circle 'D' in FIG. 22.

Referring now to FIGS. 22 to 24 of the drawings, still a further embodiment of equipment for forming a tissue prosthesis, in situ, at a site in a patient's body is illustrated. Once again, with reference to the previous drawings, like reference numerals refer to like parts, unless otherwise specified.

In this embodiment, the equipment 110 includes a stiffening element in the form of a stiffening rod or tube 160. Prior to insertion of the filler tube 114 into the envelope tube 112, the stiffening rod 160 is inserted into the passage 116 of the envelope tube 112. A distal end 162 of the stiffening rod 160 projects beyond a distal end of the envelope tube 112 and terminates at a distal wall in the interior 130 of the envelope 38. A gap 161 is created between the envelope tube 112 and the stiffening rod 160. The gap 161 and the interior 130 of the envelope 38 are evacuated by operation of the evacuation device to cause the envelope 38 to collapse on to the distal end 162 of the stiffening rod 160. This facilitates insertion of the envelope 38 into the introducer 22 and into the cavity 36 of the disc 10.

Once the envelope 38 has been located within the cavity 36, the evacuation device is turned off to release the envelope 38 from the distal end 162 of the stiffening rod 160 and this allows the stiffening rod 160 to be withdrawn. The filler tube 114 can then be inserted into the envelope tube 112, as described above, to enable filler material 60 to be charged into the envelope 38.

In another embodiment (not illustrated), the stiffening rod 160 is dimensioned to fit in the interior of the filler tube 114. With this arrangement, the gap 118 between the envelope tube 112 and the filler tube 114 is evacuated, as described above, with the stiffening rod 160 projecting through the distal end of the envelope tube 112 and the envelope 38 being collapsed over the distal end 162 of the stiffening rod 160.

A proximal end 164 of the stiffening rod carries a cap connector 166 which connects to the Y connector 134 to retain the stiffening rod 160 in position relative to the envelope tube 112 and/or the filler tube 118, as the case may be. The cap connector 166 seals hermetically against a proximal end of the Y connector to enable the gap 161 and the interior 130 of the envelope 38.

It is an advantage of the invention that a method and equipment are provided which facilitates minimally invasive formation of a tissue prosthesis in situ. In addition a tissue prosthesis is provided which is resistant to delamination. In particular, in the case where the tissue prosthesis has an envelope and filler material of the same class of material, a unified, integrated structure is provided which is resistant to delamination and relative movement between the envelope and the filler material. The unified structure and the fact that the envelope is elastically deformed and is retained under tension also renders the envelope resistant to creasing increasing the operational efficiency of the prosthesis by being better able to distribute forces to the annulus fibrosis of the disc.

In addition, the use of a silicone rubber envelope is particularly advantageous due to the fact that, when a nucleotomy has been performed, residue remains behind which is irregular in shape. It is beneficial to have a prosthesis which expands and conforms as closely as possible to the shape of the cavity in order that compressive, tensile, bending and torsional forces can be accommodated by the disc. In addition, the provision of a tissue prosthesis expanding and closely conforming to the shape of the cavity results in an improvement in stimulation and deformation of the end plates of the vertebrae and thereby aiding in restoration of the natural pumping action which assists in the influx of nutrients and the effluxion of waste products from within the disc.

It is yet a further advantage of the invention that the tissue prosthesis can be formed in situ in a minimally invasive manner. The need for invasive surgical procedures is therefore obviated and there is the added advantage of more rapid post-operative recovery and the reduced need for a prolonged period in hospital.

The equipment of the invention further provides an efficient, easy to use manner of forming the tissue prosthesis. By having the tubes etc nested, a clinician is more easily able to manipulate the equipment to place and form the tissue prosthesis.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A system for the in situ formation of a tissue prosthesis, comprising:
   an elongate introducer for defining a tool path to a prosthesis site defined by a nucleus pulposus cavity forming part of a nucleated intervertebral disc;
   said elongate introducer having a proximal end and a distal end, and having a sufficient length to be inserted percutaneously by its distal end through a pierced annulus fibrous and into abutment with the prosthesis site;
   a retaining structure disposed at the proximal end of said elongated introducer in a fixed position relative to the elongated introducer for receiving and helping to retain said elongated introducer,
   an elongate delivery device wherein the elongated introducer facilitates a delivery of a fluid filler material to the prosthesis site for the in situ formation of the tissue prosthesis;
   another retaining structure for lockingly engaging said retaining structure to said elongate delivery device in a fixed position relative to said elongate introducer;
   wherein said another retaining structure is carried at about a distal end portion of a fluid connector having a primary member and a secondary member, said primary member being fast with and in fluid communication with a passageway defined by said elongate delivery device to facilitate a concurrent delivery of said fluid filler material to a tissue prosthesis receiving cavity and a diverting of a sufficient volume of air from the tissue prosthesis receiving cavity to substantially prevent a formation of air bubbles within the tissue prosthesis during its in situ formation in the nucleus pulposus cavity;
   a dispensing device for dispensing the fluid filler material to the prosthesis site for the in situ formation of the tissue prosthesis, said dispensing device including a dispenser in fluid communication with a static mixer having a locking mechanism arranged at its distal end for lockingly coupling in fluid communication said dispensing device to said fluid connector; and
   an elongate filler tube member carried on a distal end of said static mixer enabling said elongate filler tube to be slidably received within said passageway to facilitate the charging of fluid filler material to the tissue prosthesis receiving cavity;
   wherein said elongate filler tube member has a smaller outer diameter than an inner diameter of said elongate delivery device to form an annular gap between said elongate filler tube member and said elongate delivery device;
   wherein said annular gap is in fluid communication with said secondary member to help facilitate the diverting of air from the tissue prosthesis receiving cavity as said tissue prosthesis receiving cavity is being charged with the fluid filler material; and
   an engaging member carried at a distal end of said elongate filler tube member for engaging and opening a valve carried at a distal end of said elongate delivery device, said valve providing a fluid access path to the tissue prosthesis receiving cavity and for placing the tissue prosthesis receiving cavity in fluid communication with said annular gap when said valve is in an open position.

2. The system according to claim 1, further comprising:
a removal tool mechanism mounted in a snug fit on an outer surface area of said elongate delivery device, wherein said elongate delivery device is displaceable in at least one direction along said tool path relative to said removal tool mechanism; and
wherein the distal end of said elongate delivery device has an outer diameter dimensioned to receive thereon an envelope for helping to define the tissue prosthesis receiving cavity, said envelope including an annular sleeve dimensioned to be slidably received in a snug fit on the distal end of said elongate delivery device, an envelope defining member bonded to an outer surface of the sleeve, said sleeve helping to define and retain said valve in position relative to said tissue prosthesis receiving cavity and said annular gap to facilitate providing the fluid access path to the tissue prosthesis receiving cavity and a fluid discharge path to the secondary member to establish a low pressure environment within the annular gap and the tissue prosthesis receiving cavity for substantially inhibiting the formation of air bubbles in the tissue prosthesis as filler material is charged into the tissue prosthesis receiving cavity.

3. The system according to claim 2, wherein said envelope defining member is adhesively bonded to the outer surface area of said sleeve by an annular adhesive layer.

4. The system according to claim 3, further comprising:
a gripping formation carried at about a proximal end area of said removal mechanism for slidably moving said removal mechanism along the outer surface area of said elongate delivery device a sufficient distance to engage said annular sleeve with a sufficient removal force to cause the annular sleeve to be pushed off the distal end of said elongate delivery device so that the valve defined and retained in position by said annular sleeve occludes the pierced annulus fibrous allowing the tissue prosthesis to be retained in the prosthesis site.

5. A system for the in situ formation of a tissue prosthesis, comprising:
an elongate introducer to help facilitate an implanting of the tissue prosthesis into a nucleated intervertebral disc;
said elongate introducer having a distal end for percutaneously engaging in abutment a pierced annulus fibrous forming part of the nucleated intervertebral disc to help facilitate the in situ formation of the tissue prosthesis in a nucleus pulposus cavity bounded by the pierced annulus fibrous;
said elongate introducer having a proximal end with a notched ramp-like receiving formation carried thereon to facilitate fixing said elongate introducer in position relative to an elongate delivery device;
said elongate delivery device being configured to carry on a distal end thereof a sleeve secured by an annular adhesive layer to an envelope defining member, said envelope defining member defining a tissue prosthesis receiving cavity;
a fluid coupler fixed to said elongate delivery device by a primary member forming part of said fluid coupler, said primary member being in fluid communication with a secondary member further forming part of said fluid coupler to facilitate a concurrent delivery of a fluid filler material to the tissue prosthesis receiving cavity and a diverting of a sufficient volume of air from the tissue prosthesis receiving cavity to substantially prevent a formation of air bubbles within the tissue prosthesis during its in situ formation in the nucleus pulposus cavity;
wherein a distal end of said primary member and a proximal end of said elongate delivery device are coupled in fluid communication with one another and in fluid communication with a valve defined by said sleeve, said valve when opened enabling the concurrent delivery of the fluid filler material to the tissue prosthesis receiving cavity and the diverting of air from the tissue prosthesis receiving cavity to said secondary member for creating a low pressure environment within the tissue prosthesis receiving cavity;
a clip arrangement forming a distal end portion of said primary member, said clip arrangement being dimensioned to be received within a notch forming part of said notched ramp-like receiving formation to retain said elongate delivery device in position relative to said elongate introducer;
a removal mechanism having a distal end and a proximal end, wherein the proximal of said removal mechanism carries a gripping formation to facilitate relative movement between said elongate delivery device and said removal mechanism to displace said sleeve from the distal end of said elongate delivery device after said envelope defining member has been charged with a sufficient amount of the fluid filler material to cause the envelope defining member to conform to the shape of the nucleus pulposus cavity;
wherein said sleeve when displaced from the distal end of said elongate delivery device occludes the pierced annulus fibrous substantially preventing discharge of the fluid filler material from the envelope defining member;
a locking mechanism arranged at a distal end portion of a dispensing device; said locking mechanism interlocking said dispensing device and said primary member in fluid tight engagement to facilitate a feeding of the fluid filler material to the tissue prosthesis receiving cavity via said primary member and said elongate delivery device;
wherein the proximal end of said primary member interacts with the locking mechanism carried by said dispensing device;
wherein said dispensing device includes a dispenser feeding into a static mixer, said static mixer having a distal end for carrying a filler tube having an outside diameter smaller than an inside diameter of an envelope tube forming part of said delivery device to form an elongated gap between an inside surface of said envelope tube and an outside surface of said filler tube and to establish a fluid communication path from said gap to said secondary member; and
wherein said filler tube carries at its distal end an engaging member, said engaging member for engaging and opening said valve to enable the fluid filler material to flow into the tissue prosthesis receiving cavity and to enable air to flow out of the tissue prosthesis receiving cavity to said gap to create the low pressure environment within said tissue prosthesis receiving cavity.

* * * * *